United States Patent [19]
Verdaguer et al.

[11] Patent Number: 6,072,085
[45] Date of Patent: Jun. 6, 2000

[54] IMINE HYDROSILYLATION, USES AND REAGENTS RELATED THERETO

[75] Inventors: Xavier Verdaguer, Barcelona, Spain; Udo E. W. Lange, Ludwigshafen, Germany; Stephen L. Buchwald, Newton, Mass.

[73] Assignee: Massachusetts Institute of Technology, Cambridge, Mass.

[21] Appl. No.: 08/941,627

[22] Filed: Sep. 30, 1997

[51] Int. Cl.[7] .......................... C07C 211/00; C07C 209/00
[52] U.S. Cl. .......................... 564/384; 564/386; 564/391; 564/396; 564/397
[58] Field of Search .................................... 564/384, 386, 564/391, 396, 397

[56] References Cited

U.S. PATENT DOCUMENTS

| | | | |
|---|---|---|---|
| 5,536,877 | 7/1996 | Hammer et al. | 564/386 |
| 5,536,878 | 7/1996 | Nagata et al. | 62/443 |

OTHER PUBLICATIONS

Reding, M., et al., "Short Enantioselective Total Syntheses of the Piperidine Alkaloids (S)–Coniine and (2R,6R)–trans–Solenopsin A via Catalytic Asymmetric Imine Hydrosilylation," *J. Org. Chem.*, 63, pp. 6344–6347, 1998.
Willoughby, C., et al., "Catalytic Asymmetric Hydrogenation of Imines with a Chiral Titanocene Catalyst: Kinetic and Mechanistic Investigations," *J. Am. Chem. Soc.*, 116, pp. 11703–11714, 1994.
Tani, Kazuhide, et al., "Iridium(I)–Catalyzed Asymmetric Hydrogenation of Prochiral Imines; Protic Amines as Catalyst Improvers", *Chemistry Letters*, pp. 955–956, 1995.
Becker, R. et al., "Enantioselective Hydrosilylation of Prochiral 3,4–Dihydro–2H–pyrrole Derivatives", *Agnew.Che.Int.Ed.Engl.* 24 (1985).
Bolm, C., et al., "Catalyzed Enantioselective Borane Reduction of Ketimine Derivatives", *Institut fur Organisch Chemie der Universitat Basel*, St. Johanns–Ring 19, CH–4056 B, Aug. 1994.
Burk, M.J., et al., "Preparation and Use of C2–Symmetric Bis(phospholanes): Production of cx–Amino Acid Derivatives via Highly Enantioselective Hydrogenation Reactions" *J. Am. Chem. Soc.* 115: 10125–10138 (1993).
Brockmann, M., et al., "Rhodium(I)–Mono–Und–Diazadienkomplexe, Synthese, Spektroskopische Charakterisierung, Oxidative Additionsreaktionen Und Einsatz In Der Homogenen Katalyse Zur Hydrosilylierung", *Journal of Organometallic Chemistry*, 301, 209–226 (1986).
Brunner, H., et al. "Assymetric Catalysis. 8*.X–Ray Structure Analysis of the Asymmetric Hydrosilylation Catalyst Cyclo–octa–1, 5–diene–pyrrol–2–carbald–(s)–1–phenylethyliminato–rhodium (I)", *Inorganica Chimica Acta*, 112, 65–70 (1986).
Brunner, H., et al., Asymmetric Catalysis. 29.[1] Optically Active Primary Amines by Enantioselective Catalytic Hydrosilylation of Ketoximes, *Organometallics*, 5, No. 4 (1986).

Cho, B.T., et al., "Enantioselective Synthesis of Optically Active Metolachlor via Asymmetric Reduction", *Tetrahefron: Asymmetry*, 3, No. 3, 337–340 (1992).
Cho, B.T., et al., "Asymmetric Reduction of N–Substituted Ketimines with the Reagent prepared from Borane and (S)–(–)_–2–Amino–3–methyl–1,1–diphenylbutan–1–ol (Itsuno's Reagent): Enantioselective Synthesis of Optically Active Secondary Amines", *J. Chem. Soc. Perkin Trans.*, 1 (1990).
Hong, Y., et al., "Asymmetric Reduction of a–Ketoimines with Oxazaborolidine Catalysts: A Novel, Practical Approach to Chiral Arylethanolamines", *Tetrahedron Letters*, 35, No. 31, 5551–5554 (1994).
Hutchins, O. R., et al., "Asymmetric Reduction of Phosphinyl Imines with Hydride Reagents. Enantioselective Synthesis of Chiral Primary Amines", *J. Or. Chem*, 52, 702–704, (1987).
Kagan, B. Henri, et al., "Reduction Asymetrique Catalysee Par Des Complexes De Metaux De Transition", *Journal of Organometallic Chemistry*, 90, 353–365 (1975).
Langlois, N., et al., "Synthese Asymetrique D'Amines Par Hydrosilyation D'Imines Catalysee Par Un Complexe Chiral Du Rhodium", *Tetrahedron Letters*, No. 49, 4865–4868 (1973).
Levi, A., et al., Asymmetric Reduction of Carbon—Nitrogen, Carbon—Oxygen, and Carbon—Carbon Double Bonds by Homogeneous Catalytic Hydrogenation, *J.C.S. Chem. Comm.*, (1975).
Nakagawa, M., et al., "Asymmetric Reductions of Imines and Ketones by Chiral Oxaborolidines", *Tetrahedron*, vol. 49, No. 9, pp. 1739–1748 (1993).
Ojima, I. and Kogure, T., "A Novel Method For The Reduction Of Schiff Bases Using Catalytic Hydrosilylation", *Tetrahedron Letters*, No. 27, pp. 2475–2478 (1973).
Reding, M., "An Inexpensive Air–Stable Titanium Based System for the Conversion of Esters to Primary Alcohols", *J. Org. Chem.* 60, 7884–7890 (1995).
Tillack, A., et al., "The Hydrosilylation of Ald–and Ketimines Catalyzed by Titanocene Complexes", *Tetrahedron Letters*, vol. 38, No. 9, pp. 1533–1534 (1997).
Verdaguer, X., et al., "Highly Enantioselective Imine Hydrosilylation Using (S,S)–Ethylenebis(n5–tetrahydroindenyl) titanium Difluoride", *J. Am. Chem. Soc.* 118, 6784–6785 (1996).
Willoughby, A. C., et al., "Preparation of Novel Titanium Complexes Bearing 0–Phosphinophenol Ligangs", *Organometallics*, 15 472–475 (1996).
Willoughby, A. C. et al., "Catalytic Asymmetric Hydrogenation of Imines with a Chiral Titanocene Catalysts: Scope and Limitations", *J. Am. Chem. Soc.*, 116, 8952–8965 (1994).

(List continued on next page.)

*Primary Examiner*—Paul F. Shaver
*Attorney, Agent, or Firm*—Matthew P. Vincent; Dana M. Gordon; Foley, Hoag & Eliot LLP

[57] ABSTRACT

The method of the present invention provides a simple general route to a wide range of secondary amines.

24 Claims, No Drawings

OTHER PUBLICATIONS

Wright, E. M. and Svejda A.S., "Synthesis of optically active Schiff base ligands from chiral 6–alkoxy–2–pyridinecarboxaldehydes and their application in rhodium catalyzed hydrosilations", *Inorganica Chimica Acta,* 175, 13–15 (1990).

Yamada, K. et al., "A Novel Asymmetric Reduction of Imines with Chiral Sodium Triacyloxyborohydrides",*Tetrahedron Letters,* vol. 22, No. 39, pp. 3869–3872 (1981).

Zassinovich, G. and Grisoni, F., "Enantioselective Transfer Hydrogenation of Ketones Catalyzed By Rhodium (I) Compexes Of Chiral Schiff Bases", *Journal of Organometallic Chemistry,* 247, C24–C26 (1983).

IMINE HYDROSILYLATION, USES AND REAGENTS RELATED THERETO

This invention was made with government support under Grant number NIH-2R01-GM46059 awarded by the National Institutes of Health. The government has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46–79) include fewer side effects and greater potency of enantiomerically pure compounds.

Traditional methods of organic synthesis have often been optimized for the production of racemic materials. The production of enantiomerically pure material has historically been achieved in one of two ways: use of enantiomerically pure starting materials derived from natural sources (the so-called "chiral pool"), or resolution of racemic mixtures by classical techniques. Each of these methods has serious drawbacks, however. The chiral pool is limited to compounds found in nature, so only certain structures and configurations are readily available. Resolution of racemates requires the use of resolving agents, which may be inconvenient and time-consuming. Furthermore, resolution often means that the undesired enantiomer is discarded, thus wasting half of the material.

With new drug development and sales of single enantiomer products advancing, the push to strengthen capabilities in asymmetric synthesis and chiral kinetic resolution is intensifying.

SUMMARY OF THE INVENTION

The method of the present invention provides a simple general route to a wide range of seconary amines. Addition of primary amines to the hydrosilylation reaction of N-substituted imines greatly increases the scope of the metal-catalyzed asymmetric reduction of imines. An important added feature of this method is that chiral secondary amines can be obtained in much higher optical purity than would be predicted by the E/Z ratios of the starting imines.

DETAILED DESCRIPTION OF THE INVENTION

The demand for enatiomerically pure secondary amines has prompted a great effort in the development of catalytic processes for the asymmetric hydrogenation and hydrosilylation of imines (refs 1–3). We have recently reported a highly enantioselective titanium-catalyzed hydrosilylation of imines (ref 4). This method involved, e.g., the treatment of (S,S)-ethylene-bis($\eta^5$-tetrahydroindenyl)titanium difluoride with phenylsilane (refs 4,6), which yields a very active catalytic system for the hydrosilylation of N-methyl and cyclic imines. See Equation 1.

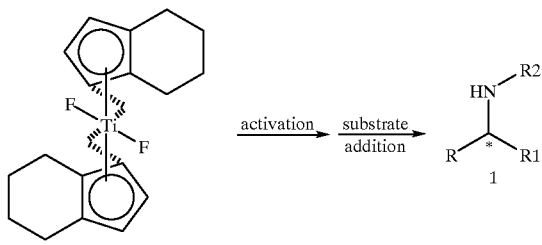

Equation 1

The rate-determining step in the titanium-catalyzed hydrogenation of imines has been proposed to be cleavage of the Ti—N bond in the intermediate amido complex via a σ-bond metathesis pathway (ref 7); we believe a similar situation holds for the hydrosilylation reaction. Specifically, for imine substrates with moderate to large nitrogen substituents, the rate of Ti—N cleavage is very slow.

We have discovered that the addition of a nucleophilic additive to the reaction mixture, e.g., an additive which could convert the titanium-amido (T-A) intermediate into a more reactive complex, yet one which can removed by the silane to recycle the catalyst, leads to a synthetic scheme with increased substrate range. As set forth with greater detail below, the subject method can be generally described as combining, in a reaction mixture, a substrate imine, a nucleophilic activator, a silane, and a metal catalyst under conditions wherein the reactants and catalyst promote the reduction of the imine double bond. Generally, the substrate imine, nucleophilic activator and silane are provided in stoichiometric (or greater) amounts, and the metal catalyst is provided in catalytic amounts.

In preferred embodiments, the substrate imine is an imine of ketone, and the reaction can be enantioselective, e.g., by use of an asymmetric catalyst.

There are several salient features to the subject method which can be appreciated by those skilled in the art. For instance, in general the subject reaction can be performed at lower temperatures and/or pressures than, for example, hydogenation reactions yielding similar products. See, for example, Willoughby et al. (1994) *JACS* 116:11703. Thus, the subject reaction is more amenable to use of reactants or products which include sensitive functionalities, e.g., which would otherwise be labile under harsh reaction conditions.

Another feature to the subject method is that, in general, the yield and/or enantioselectivity of the subject reaction is not apparently effected by the E/Z ratio for isomers in the substrate imine starting material. This can provide a significant advantage for those instances, e.g., where an isomerically pure starting material is unavailable or prohibitively expensive.

Still another feature of the present method can be realized in those embodiments which utilize a polymeric silane, such as PMHS. Many polymeric silanes are readily available, and often inexpensive. These forms of silanes also provide a means for separating reaction product from silane by-products.

The ability to provide an imine hydosilylation synthesis scheme which can be carried out to produce secondary amines, especially if carried out in an enantioselective manner, has broad application, especially in the agricultural and pharmaceutical industries, as well as in the polymer industry.

Definitions

For convenience, before further description of the present invention, certain terms employed in the specification, examples, and appended claims are collected here.

The term "substrate imine" group refers to an N-substituted imine which is susceptible to the subject hydrosilylation reaction. The substrate imine can be, e.g., an imine of a ketone or an imine of aldehyde.

The term "nucleophile" is recognized in the art, and as used herein means a chemical moiety having a reactive pair of electrons. Examples of nucleophiles include uncharged compounds such as alcohols, thiols, selenol, and amines, and charged moieties such as alkoxides, thiolates, carbanions, and a variety of other organic anions.

The term "reaction product" means a compound which results from the reaction of reduction of the substrate imine group, e.g., a compound which includes a secondary amine. In general, the term "reaction product" will be used herein to refer to a stable, isolable amines, and not to unstable intermediates or transition states.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioform ate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino., azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art recognized and refer to both unsubstituted and substituted amines, e.g., a moiety that can be represented by the general formula:

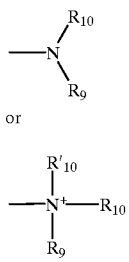

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

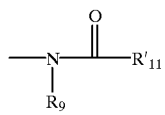

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

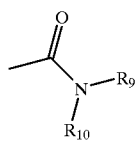

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

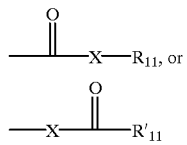

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R'$_{11}$ is hydrogen, the formula represents a "thiolcarboxylic acid." Where X is a sulfur and R$_{11}$ is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

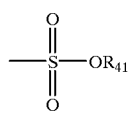

in which R$_{41}$ is an electron pair, hydrogen, alkyl, cycloalkyl, or aryl.

The term "sulfate" is art recognized and includes a moiety that can be represented by the general formula:

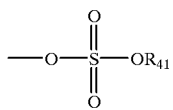

in which $R_{41}$ is as defined above.

The term "sulfonamido" is art recognized and includes a moiety that can be represented by the general formula:

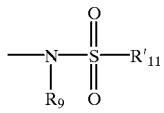

in which $R_9$ and $R'_{11}$ are as defined above.

The term "sulfamoyl" is art-recognized and includes a moiety that can be represented by the general formula:

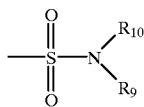

in which $R_9$ and $R_{10}$ are as defined above.

The terms "sulfoxido" or "sulfinyl", as used herein, refers to a moiety that can be represented by the general formula:

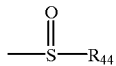

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

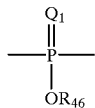

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

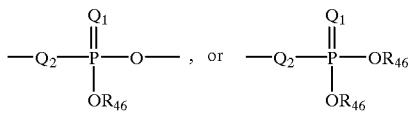

wherein $Q_1$ represented S or O, and each $R_{46}$ independently represents hydrogen, a lower alkyl or an aryl, $Q_2$ represents O, S or N. When Q, is an S, the phosphoryl moiety is a "phosphorothioate".

A "phosphoramidite" can be represented in the general formula:

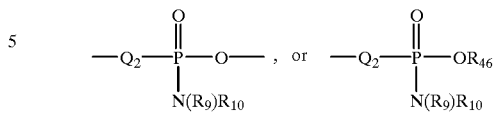

wherein $R_9$ and $R_{10}$ are as defined above, and $Q_2$ represents O, S or N.

A "phosphonamidite" can be represented in the general formula:

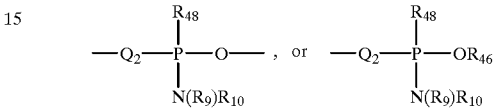

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and 13 Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Exemplary Catalyzed Reactions

As described above, one aspect of the Applicants' invention features a general hydrosilylation reaction which comprises combining, in a reaction mixture, a substrate imine, a nucleophilic activator, a silane, and a metal catalyst under conditions wherein the reactants and catalyst promote the reduction of the imine double bond. While the substrate imine can be an imine of an aldehyde, a important benefit of the reaction can be realized, namely the asymmetric reduction of an imine, when the substrate imine is an imine of ketone, and the reaction uses an asymmetric catalyst.

The primary constituents of the method, set out in more detail below, are a metal catalyst, preferably of asymmetric geometry; a prochiral "substrate" having an imine group, the carbon of which is a prochiral carbon center; a silane hydride or compound capable of producing a silane hydride under the reaction conditions; and a nucleophilic activator.

Turning first to the substrate imine. In general, the substrate imine can be a compound which includes an N-substituted imine, and can be an acyclic or cyclic imine. The substrate imine can be an imine of aldehyde, but is preferably an imine of a ketone in order to take advantage of the asymmetric induction capabilities of the present reaction.

In preferred embodiments, the substrate imine can be represented in the general formula:

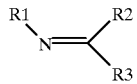

wherein
R1, R2 and R3 each independently represent an alkyl (preferably a lower alkyl), an alkenyl (preferably a lower alkenyl), an alkynyl (preferably a lower alkynyl), a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S-lower alkenyl, —$(CH_2)_m$—S—$(CH_2)_n$—R8, or protecting groups of the above or a solid or polymeric support; $R_8$ represents a substituted or unsubstituted aryl, aralkyl, cycloalkyl, cycloalkenyl, or heterocycle; or one of R2 or R3 can be a hydrogen; or R2 and R3, taken together with the imine carbon, can form a substituted or unsubsitituted ring, which ring may be a carbocycle or heterocycle, monocyclic or polycyclic;

and n and m are independently for each occurrence zero or an integer in the range of 1 to 6.

In preferred embodiments, R1, R2 and R3 each represent an alkyl, akenyl, akynyl, —$(CH_2)_m$—$R_8$.

In preferred embodiments, R2 and R3 are different, e.g., so that resulting amine includes an adjacent chiral carbon center.

In preferred embodiments, the N-substituent R1 will not form a conjugated system with the imine double bond, e.g., R1 will not include any unsaturated bonds less than two bonds from the imine nitrogen. In even more preferred embodiments, R1 can be an alkyl or —$(CH_2)_m$—$R_8$.

In other embodiments, the substrate imine can be a cyclic imine, e.g., represented in the general formula:

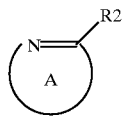

wherein
A represents a substituted or unsubstituted ring selected from a group consisting of a cycloalkyl, a cycloakenyl, an aryl, and a heterocyclic ring, or a polycyclic combination thereof;

R2 is a hydrogen, though more preferably represents an alkyl (preferably a lower alkyl), an alkenyl (preferably a lower alkenyl), an alkynyl (preferably a lower alkynyl), a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S-lower alkenyl, —$(CH_2)_m$—S—$(CH_2)_n$—R8, or protecting groups of the above or a solid or polymeric support; $R_8$ represents a substituted or unsubstituted aryl, aralkyl, cycloalkyl, cycloalkenyl, or heterocycle;

and n and m are independently for each occurrence zero or an integer in the range of 1 to 6.

In preferred embodiments, R2 represents an alkyl, akenyl, akynyl, —$(CH_2)_m$—R8.

In preferred embodiments, the ring A does not form a conjugated system with the imine double bond, e.g., the ring will not include any unsaturated bonds less than two bonds from the imine nitrogen.

In one illustrative embodiment, the substrate imine is an N-benzyl amine, N1,1-diphenyl-1-ethanimine, which can be reduced by the subject method to yield a chiral amine.

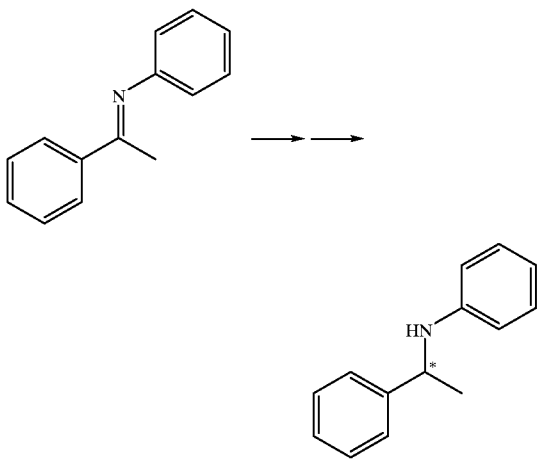

In still another illustrative embodiment, the subject method can be used for the asymmetric reduction of an N1-phenyl-1-indanimine.

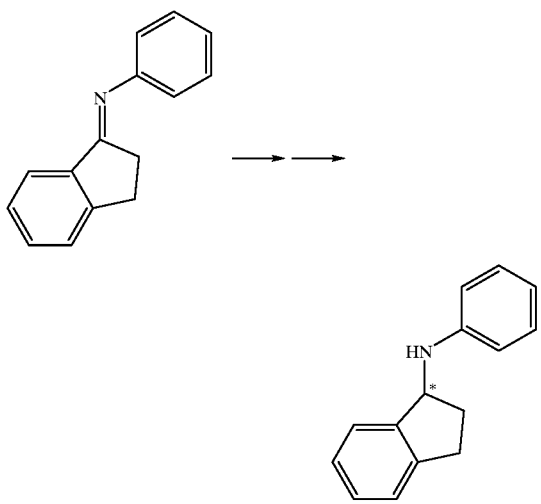

In yet another illustrative embodiment, the subject method can be used for the asymmetric reduction of a cyclic imine such as 2-phenylpyrroline.

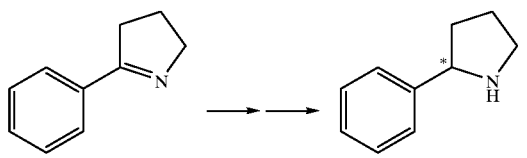

The nucleophilic activator which is used in the subject method will generally be a compound that includes a nucleophilic moiety which, under the reaction conditions, is a strong enough Lewis base to replace an intermediate amide group between the substrate imine nitrogen and the metal center of the catalyst. Preferably, the metal-activator complex is more thermodynamically favorable than then metal-intermediate amide complex. However, the metal-activator complex must be removable from the silane, e.g., the nucleophilic activator does not form so strong a bond with the metal that it cannot be replaced by hydride (i.e. from the silicon hydride). Preferably the reaction rate for the removal of the activator intermediate from the catalyst by the hyride is faster than the rate of removal of the substrate intermediate from the catalyst by the hyride.

As set out above, the term "Lewis base" refers to any chemical species which is an electron pair donor. Two-electron Lewis bases are those bases which may donate a single pair of electrons. The types of Lewis base functional groups capable of forming coordinate complexes with the metal catalysts are too numerous to categorize, though in preferred embodiments the nucleophilic activator will include atoms from Periodic Groups 15 and 16.

Lewis bases from Group 15 contain nitrogen, phosphorous, arsenic, antimony or bismuth atoms as electron pair donors. Preferable Lewis bases from Group 15 contain nitrogen, phosphorous, and antimony, and more preferably, nitrogen or phosphorous.

Lewis bases from Group 16 contain oxygen, sulfur, or selenium atoms as electron pair donors. Preferable Lewis bases from Group 16 contain oxygen or sulfur.

Exemplary Lewis basic moieties which can be used in the nucleophilic activator include amines (primary, secondary, and tertiary) and aromatic amines, amino groups, amido groups, nitro groups, nitroso groups, amino alcohols, nitrites, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

In preferred embodiments, the nucleophilic activator includes a Lewis basic nitrogen which can form an intermediate metal bond with ithe metal center of the catalyst. In principle, the bind between the metal and the nitrogen of the substrate imine should be the same strength as that with the nitrogen of the activator. Thus, the lack of steric hinderance can be the thermodynamic force driving the reaction towards replacement of the substrate-metal complex with the activator-metal complex.

Even more preferably, the activator is an amine, e.g., a primary amine represented by the general formula:

$H_2N-R4$ wherein

R4 represents an alkyl (preferably a lower alkyl), an alkenyl (preferably a lower alkenyl), an alkynyl (preferably a lower alkynyl), a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a sulfonyl, a sulfoxido, a sulfate, a sulfonate, a sulfamoyl, a sulfonamido, a phosphoryl, a phosphonate, a phosphinate, —$(CH_2)_m$—R8, —$(CH_2)_m$—OH, —$(CH_2)_m$—O-lower alkyl, —$(CH_2)_m$—O-lower alkenyl, —$(CH_2)_m$—O—$(CH_2)_n$—R8, —$(CH_2)_m$—SH, —$(CH_2)_m$—S-lower alkyl, —$(CH_2)_m$—S-lower alkenyl, —$(CH_2)_m$—S—$(CH_2)_n$—R8, or protecting groups of the above or a solid or polymeric support; $R_8$ represents a substituted or unsubstituted aryl, aralkyl, cycloalkyl, cycloalkenyl, or heterocycle;

and n and m are independently for each occurrence zero or an integer in the range of 1 to 6.

Preferably R4 has a smaller steric volume than R2 and R3 of the substrate imine, and is more preferably selected to minimize the steric volume within two bonds of the amine nitrogen. For instance, R4 is preferably an alkyl, such as a primary or secondary alkyl.

As described below, the silane regenerates the catalyst. In preferred embodiments, the silane is represented by the general formula (R6—)(R7—)R8—SiH, wherein of R6 represents an alkyl (preferably a lower alkyl), an alkenyl (preferably a lower alkenyl), an alkynyl (preferably a lower alkynyl), a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or protecting groups of the above or a solid or polymeric support; R$_8$ represents a substituted or unsubstituted aryl, aralkyl, cycloalkyl, cycloalkenyl, or heterocycle;

R7 and R8 each independently represent hydrogen or an alkyl (preferably a lower alkyl), an alkenyl (preferably a lower alkenyl), an alkynyl (preferably a lower alkynyl), a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a sulfonyl, a sulfoxido, a sulfate, a sulfonate, a sulfamoyl, a sulfonamido, a phosphoryl, a phosphonate, a phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, or protecting groups of the above or a solid or polymeric support; R$_8$ represents a substituted or unsubstituted aryl, aralkyl, cycloalkyl, cycloalkenyl, or heterocycle; and n and m are independently for each occurrence zero or an integer in the range of 1 to 6.

In preferred embodiments, the silane is a hydromonosilane, e.g., wherein R7 and R8 represent hydrogen. Even more preferable are hydromonosilates wherein R6 represents a lower alkyl, lower akenyl or lower aryl.

Thus, the subject method can be carried out with hydromonosilanes, hydrodisilanes, hydrotrisilanes or mixtures of two or more thereof. Examples of the hydromonosilanes are silane, methylsilane, ethylsilane, n-propylsilane, (3,3,3-trifluoropropyl)silane, n-butylsilane, tert-butylsilane, (1-methylpropyl)silane, (2-methylpropyl)silane, amylsilane, n-hexylsilane, cyclohexylsilane, n-heptylsilane, n-octylsilane, n-nonylsilane, n-decylsilane, n-dodecylsilane, phenylsilane, p-tolylsilane, mesitylsilane, benzyl silane, phenetylsilane, (trimethylsilylmethyl)silane, dimethylsilane, diethylsilane, di-n-propyl silane, bis(3,3,3-trifluoropropyl) silane, di-n-butylsilane, di-tert-butylsilane, di(1-methylpropyl)silane, di(2-methylpropyl)silane, diamylsilane, di-n-hexylsilane, dicyclohexylsilane, di-n-heptylsilane, di-n-octylsilane, di-n-nonylsilane, di-n-decylsilane, di-n-dodecylsilane, diphenylsilane, di-p-tolylsilane, dimethylsilane, dibenzylsilane, diphenetylsilane, bis(trimethylsilylmethyl)silane, ethylmethylsilane, methyl-n-propylsilane, methyl(3,3,3-trifluoropropyl)silane, methyl-i-propylsilane, n-butylmethylsilane, tert-butylmethylsilane, methyl(I-methylpropyl)silane, methyl(2-methylpropyl) silane, arriylmethylsilane, n-hexylmethylsilane, cyclohexylmethylsilane, n-heptylmethylsilane, methyl-n-octylsilane, methyl-n-nonylsilane, n-decylmethylsilane, n-dodecylmethylsilane, methylphenylsilane, p-tolylmethylsilane, methylmesitylsilane, benzylmethylsilane, methylphenetylsilane, methyl (trimethylsilylmethyl)silane, (p-methylphenetyl)silane, ethylphenylsilane, and tert-butylphenylsilane.

In one embodiment, the metal catalyst is one which has asymmetric ligands (a "chiral catalyst") and can reduce the substrate imine in an enantioselective manner. The metal center of the catalyst is preferably a transition metal, and even more preferably is a group IV metal, e.g., titanium, zirconium, hafnium, iron, ruthenium, or vanadium, and even preferably zirconium, titanium, or hafnium, and most preferably titanium.

The ligand of the metal catalyst is preferably selected to provide a metallocene catalyst, e.g., a carbon-bridged biscyclopentadienyl metallocene. For instance, the metal catalyst can be represented by the general formula ML[x], wherein M is transition metal, x is the valence of the transition metal, and each L is individually selected and is a hydrocarbyl group containing 1 to 12 carbon atoms, alkoxy group containing 1 to 12 carbon atoms, aryloxy group containing 6 to 12 carbon atoms, halogen, hydrogen, amido, or a ligand containing at least one cyclopentadienyl-type group.

Cyclopentadienyl-type groups, as used herein, are unsubstituted cyclopentadienyl, substituted cyclopentadienyl, unsubstituted indenyl, substituted indenyl, unsubstituted fluorenyl, or substituted fluorenyl. The substituents can be any substituent known in the art which does not interfere with the reaction, for example hydrocarbyl groups containing 1 to 12 carbon atoms, alkoxy groups containing 1 to 12 carbon atoms, silyl groups, alkyl halide groups where the alkyl contains 1 to 12 carbon atoms, or halogen. Typical substituents include methyl, ethyl, propyl, butyl, amyl, isoamyl, hexyl, isobutyl, heptyl, octyl, nonyl, decyl, cetyl, 2-ethylhexyl, methoxy, ethoxy, propoxy, butoxy, chlorine, bromine, iodine, phenyl, phenoxy, dimethylsilyl, trimethylsilyl, chloromethyl, chloroethyl, and bromopropyl. Preferably the substituents are alkyl groups containing 1 to 10 carbon atoms, and more preferably 1 to 6 carbon atoms.

Typical examples of cyclopentadienyl-type groups include methylcyclopentadienyl, n-butylcyclopentadienyl, di(tert-butyl)cyclopentadienyl, tri(tert-butyl) cyclopentadienyl, pentamethylcyclopentadienyl, 1-methylindenyl, 4,7-dimethylindenyl, 4-methyl-7-(1-propyl)indenyl, 4-ethyl-7-(1-propyl)indenyl, 4-methyl-7-(1-pentyl)indenyl, 4-ethyl-7-(1-pentyl)indenyl, (1-tert-butyl) fluorenyl, (2-ethyl)fluorenyl, (2-tert-butyl)fluorenyl, (4-tert-butyl)fluorenyl, (1-methyl)fluorenyl, (9-methyl)fluorenyl, (9-tert-butyl)fluorenyl, (4-methyl)fluorenyl, 2,7-bis(tert-butyl)fluorenyl, 2,7-bis(tert-butyl)-4-(methyl)fluorenyl, benzyl fluorene, and benzyl indene.

Examples of carbon-bridged biscyclopentadiene compounds of the formula I are: 2,2-bisindenylpropane, 2,2-bisindenylbutane, 2,2-bisindenylmethane, 2,2-bisindenylcyclopentane, 2,2-bisindenylcyclohexane, 1,1-bisindenyl-1-phenyl-ethane, 1,1-bisindenylethane, 1,1-bisindenylpropane, 2,2-bis(2'-methyl-4'-phenylindenyl) propane, 2,2-bis(2'-ethyl-4'-phenyl-indenyl)propane, 2,2-bis (:2'-methyl-4'-naphthylindenyl)propane, 2,2-bis(2'-methyl-4',5'-benzoindenyl)propane, 1,1-bis(2'-methyl-4'-phenylindenyl)-1-phenylethane, 1,1-bis(2'-ethyl-4'-phenylindenyl)-1-phenylethane, 1,1-bis(2'-methyl-4'-naphthylindenyl)-1-phenylethane, 2,2-biscyclopentadienylbutane, 2,2-bis(methylcyclopentadienyl)propane, 2-cyclopentadienyl-2-fluorenylpropane, 2-(3'-methylcyclopentadienyl)-2-fluorenylpropane, 2-indenyl-2-indenyl-2-fluorenylpropane, 2-cyclopentadienyl-2-indenylpropane, 1-cyclo-pentadienyl-1-fluorenyl-1-phenylethane, 1-indenyl-1-fluorenyl-1-phenylethane, 2-(3'-tert-butylcyclopentadienyl)-2-fluorenylpropane, 1-cyclopentadienyl-1-indenyl-1-phenylethane.

Examples of suitable metallocene compounds include bis(cyclopentadienyl)zirconium dichloride, bis(cyclopentadienyl)zirconium dibromide, bis(cyclopentadienyl)zirconium diiodide, bis(methylcyclopentadienyl)zirconium dichloride, bis(n-butylcyclopentadienyl)zirconium dichloride, bis(cyclopentadienyl)hafnium dichloride, bis(cyclopentadienyl)hafnium dibromide, bis(cyclopentadienyl)hafnium diiodide, bis(methylcyclopentadienyl)hafnium dichloride, bis(n-butylcyclopentadienyl)hafnium dichloride, bis(cyclopentadienyl)titanium dichloride, bis(methylcyclopentadienyl)titanium dichloride, bis(n-butylcyclopentadienyl)titanium dichloride, bis(cyclopentadienyl)zirconium methyl chloride, bis(methylcyclopentadienyl)zirconium ethyl chloride, bis(n-butylcyclopentadienyl)zirconium phenyl chloride, bis(cyclopentadienyl)hafnium methyl chloride, bis(methylcyclopentadienyl)hafnium ethyl chloride, bis(n-butylcyclopentadienyl)hafnium phenyl chloride, bis(cyclopentadienyl)titanium methyl chloride, bis(methylcyclopentadienyl)titanium ethyl chloride, bis(n-butylcyclopentadienyl)titanium phenyl chloride, bis(cyclopentadienyl)zirconium dimethyl, bis(methylcyclopentadienyl)zirconium dimethyl, bis(n-butylcyclopentadienyl)zirconium dimethyl, bis(cyclopentadienyl)hafnium dimethyl, bis(methylcyclopentadienyl)hafnium dimethyl, bis(n-butylcyclopentadienyl)hafnium dimethyl, bis(cyclopentadienyl)titanium dimethyl, bis(methylcyclopentadienyl)titanium dimethyl, bis(n-butylcyclopentadienyl)titanium dimethyl, pentamethylcyclopentadienyl titanium trichloride, pentaethylcyclopentadienyl zirconium trichloride, pentaethylcyclopentadienyl hafnium trichloride, bis(pentamethylcyclopentadienyl)titanium diphenyl, bis(indenyl)hafnium dichloride, bis(indenyl)titanium diphenyl, bis(indenyl)zirconium dichloride, bis(fluorenyl)zirconium dichloride, bis(1-methylfluorenyl)zirconium dichloride, and mixtures thereof.

However, it will be apparent that the subject rejection need not be provided with a chiral catalyst. Thus, for example, a metallocene catalyst can be provided as isomerically pure, or as a racemic mixture. In instances of tihe latter, the reaction will generally not be enantioselective. However, an increase in reaction rate or efficienct may be sufficient motivation to reducing an imine by the subject reaction.

As is clear from the above discussion, the products which may be produced by the subject hyrosilylation reaction of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of ketones by esters, acylation of amines and the like.

Reaction Conditions

The hydrosilylation reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include alcohols such as methanol, ethanol, isopropanol, t-butanol; ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

Combinatorial Libraries

The subject hydrosilylation reaction readily lends itself to the creation of combinatorial libraries of secondary amines for the screening of pharmaceutical, agrochemical or other biological or medically-related activity or material-related qualities. A combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate biological, pharmaceutical, agrochemical or physical property is done by conventional methods.

Diversity in the library can be created at a vareity of different levels. For instance, the substrate imine groups used in the combinatorial reactions can be diverse in terms of the substituents, e.g., a vareigation in terms of the imine carbon and nitrogen substituents.

Diversity can also be introduced at the level of stereochemistry, e.g., at the chiral center created in the subject reaction. In one embodiment, one portion of the library is reduced by the subject method using one enantiomer of a chiral catalyst, while another portion of the library is similarly treated with the opposite enantiomer. The resulting library will thus include both orientations about the chiral carbon, the stereochemistry being introduced in a controlled (and taggable) manner.

A variety of techniques are available in the art for generating combinatorial libraries of small organic molecules such as the subject amines. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject amines can be synthesized and screened for particular activity or property.

Exemplfication

The invention now being generally described, it will be more readily understood by reference to the following examples which are included merely for purposes of illustration of certain aspects and embodiments of the present invention, and are not intended to limit the invention.

As set out above, we have discovered that the addition of a nucleophilic additive to the hydrosilylation reaction of imines leads to a synthetic scheme with increased substrate range.

Several amines, alcohols and thiols were tested as additives. Among these, primary amines had the most pronounced effect on the reaction. For example, use of our standard reaction protocol (see Table 2) with N-benzyl-1-indanimine 4 was ineffective, with only 5% conversion to product observed after 24 h (Table 1, entry 4) at 60 C. In contrast, slow addition of 4 equivalents of n-hexylamine to the hydrosilylation reaction mixture (eq 1) at 60 C. resulted in complete reduction of 4 in 2 h (Entry 5). Using 4 as the test substrate, we studied the influence of the nature of the added amine on the outcome of the reaction. Bulky primary amines ($^t$BuNH$_2$) and secondary amines were shown to be ineffective (entries 6 and 7). The use of isobtylamine generally gave the best results; a good reaction rate was observed and the highest enantioselectivity was realized (entry 8). (±)-Sec-butylamine (entry), in spite of providing a lower ee in the reduction of 4, was also shown to be a useful promoting agent (vide infra).

The results for the reduction of a series of acyclic imines and the details of this new protocol are depicted in Table 2. An important feature of this system, in comparison to the corresponding hydrogenation using the Brintzinger-type catalyst, is the significantly higher level of enantioselectivity realized in the reduction of acyclic imines.[10] The amine products are obtained, in general, with 91–99% ee. Of major significance is that the enantiomeric excesses of the products do not correlate with the anti/syn ratio of the starting imines, as was the case with the earlier hydrogenation.[11] The most dramatic examples of this behavior is seen for entries 8 and 9; while the corresponding imines exist as 2.5/1 and 1.8/1 mixtures of E/Z isomers, the titanocene-catalyzed reduction provides the product amines with 93 and 97% e.e., respectively. At present we have no explanation for these results, although labeling studies rule out the involvement of enamine intermediates. An additional practical aspect of the amine-promoted protocol is that it allows the use of PMHS, an inexpensive and conveniently use silane[12] as the stoichiometric reductant.[13] Usual catalyst loadings range from 0.5–1 mol %. We have demonstrated that lowering the amount of catalyst to 0.05 mol % compromises neither the yield nor the enantioselectivity of the reaction (Entry 5). We found that slow addition (syringe pump) of the primary amine (1.5–4 equiv.) to the reaction mixture is essential to achieve complete reduction of the starting imine. After complete consumption of the imine, an acidic workup yields the chiral product amines in high yields and >95% purity (GC and $^1$H NMR).

Although a detailed mechanistic study has not yet been undertaken, preliminary experiments are in accord with the catalytic cycle shown in Scheme 1. The product amines are obtained with the same absolute configuration as for the titanium-catalyzed hydrogenation, which suggests a chirality transfer step where the imine inserts into the Ti—H bond of the titanocene hydride 5, in analogy with the hydrogenation case.[7] The additive would then react with the sterically encumbered titanium-amido complex 6 to afford the product chiral amine and generate a new amido complex 7. Finally, reaction of the less hindered complex 7 with silane regenerates the titanium hydride 5. When PMHS is used as the hydride source, the $^1$H NMR spectrum of the crude product (no workup), shows free product amine while the isobutylamine additive is attached to the siloxane polymer. The proposed catalytic cycle can also explain why slow addition of the additive is required. In a competing process with the imine, the promoter can also react with titanocene hydride 5 to generate 7 with concomitant loss of hydrogen (Scheme 1b). Further reaction of 7 with silane affords the silylated primary amine. When the primary amine is present in high concentrations, this alternative reaction pathway becomes an important side reaction.

Scheme 1
Proposed catalytic cycle for amine promoted asymmetric hydrosilylation.

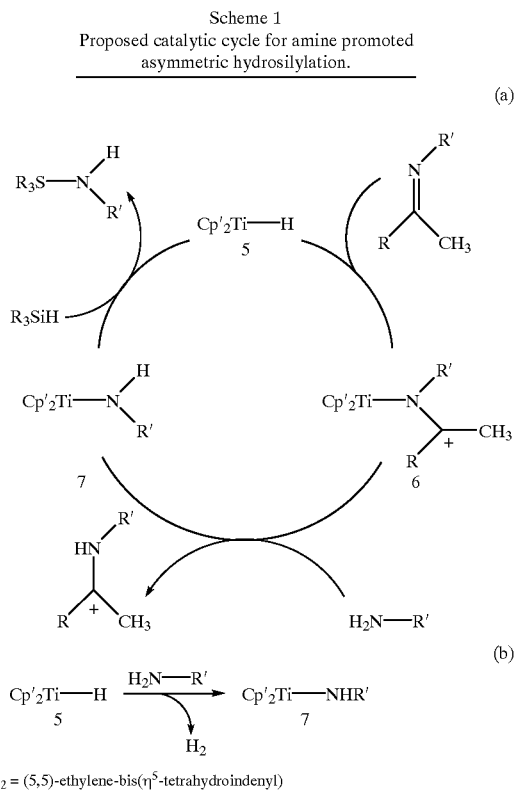

Cp'₂ = (5,5)-ethylene-bis(η⁵-tetrahydroindenyl)

In summary, we have demonstrated that the use of primary amines as additives in the titanium-catalyzed asymmetric hydrosilylation of imines greatly expands the scope of the reaction. Using PMHS, a convenient and inexpensive hydride source, this new protocol allows the preparation of a wide array of highly enantiomerically enriched secondary amines. Of significance is that the enantioselectivities obtained are not limited by the E/Z ratio of the starting imine. In addition, this work represents the first application, that we are aware of, in which an achiral nucleophilic promoter/catalyst is used to enhance the efficacy of a catalytic asymmetric reaction.[8,14] Further work to clarify the mechanism of this transformation and its application to other asymmetric processes is underway in our laboratory.

Experimental

Typical experimental procedure: A dry resealable Schlenk flask under argon was charged with (S,S-(EBTHI) TiF₂ (9 mg, 0.025 mmol) and 1 mL of dry THF. The resulting yellow solution was heated to 60 C. and PhSiH₃ (12 μL, 0.1 mmol), piperidine (9 μL, 0.1 mmol) and methanol (4 μL, 0.1 mmol) were added via syringe. The mixture was stirred at 60 C. for 15–20 min, resulting in a color change from yellow to green. At this point, THF (1 mL) and PMHS (1.65 mL, 27 mmol) were added via syringe. The sealed Schlenk flask was then removed from the oil bath, cooled to room temperature, and brought into an argon filled glovebox. N-Benzyl-1-indanimine (0.64 g, 2.7 mmol) was added, and the reaction mixture was heated to 65 C. and the color of the reaction mixture changed to brown. To this solution, isobutylamine (0.6 mL, 6 mmol) was added during a period of 2.5 h (0.25 mL/h flow rate) using a syringe pump. When the amine addition was finished, the color of the reaction mixture had changed from brown to green, and analysis by GC showed complete consumption of the starting material. The reaction mixture was cooled to room temperature, removed from the glovebox, diluted with Et₂O (30 mL) and stirred with 1 M HCl (15 mL) for 0.5 h (caution: vigorous bubbling). The aqueous layer was separated, made basic with 3 M NaOH and extracted with ether. The combined ether layers were dried (MgSO₄) and concentrated in vacuo to afford 611 mg of (+)-N-benzylindan-1-amine (95% yield, 92% ee). Note: The amine promoter could be added portionwise, by syringe, in the case of more reactive substrates or when using a higher catalyst loading. For reactions using b 1mol % catalyst, amine addition was performed in a hood under argon in a septum-capped Schlenk flask.

[1]. For a review on the asymmetric preparation of amines see: A. Johansson, Contemp. Org. Synth. 1995, 2, 393–406.

[2]. a) N. Uematsu; A. Fujii; S. Hashiguchi; T. Ikariya; R. Noyori, J. Am. Chem. Soc. 1996, 188, 49116–4917 and references therein. b) J. M. Burlak; J. A. Osbom, Organometallics 1996, 15, 3161–3169. c) M. J. Burk; J. E. Feaster, J. Am. Chem. Soc. 1992, 114, 6266–6267. d) P. Schnider; G. Koch; R. Prétôt; G. Wang; F. M. Bohnen; C. Kruger; A. Pfaltz, Chem. Eur. J. 1997, 3, 887–892.

[3]. a) R. Becker; H. Brunner; S. Mahboobi; W. Wiegrebe, Angew. Chem., Int. Ed. Engl. 1985, 24, 995–996. Angew. Chem. 1985, 97, 989–970. b) H. B. Kagan; N. Langlois; T. P. Dang, J. Organomet. Chem. 1975, 90, 353–365. c) I. Ojima; T. Kogure; Y. Nagai, Tetrahedron Lett. 1973, 14, 2475–2478. d) A. Tillack; C. Lefeber; N. Peulecke; D. Thomas; U. Rosenthal, Tetrahedron Lett. 1997, 38, 1533–1534.

[4]. X. Verdaguer; U. E. W. Lange; M. T. Reding; S. L. Buchwald, J. Am. Chem. Soc. 1996, 118, 6784–6785.

[5]. (S,S)-(EBTHI) TiF₂ is a crystalline, air-stable yellow-orange solid and can be prepared from the corresponding dichloride derivative in one step, see: (a) A. Schafer; E. Karl; L. Zsolnai; H. Gottfried; H. H. Brintzinger, J. Organomet. Chem. 1987, 328, 87–99. (b) B. Chin; S. L. Buchwald, J. Org. Chem. 1996, 61, 5650–5651. (c) P. M. Bruce; B. M. Kingston; M. F. Lappert; T. R. Spalding; R. C. Srivastava, J. Chem. Soc. (A), 1969, 2106–2110.

[6]. A faster rate of activation is observed in the presence of piperidine and MeOH.

[7]. C. A. Willoughby; S. L. Buchwald, J. Am. Chem. Soc. 1994, 116, 11703–11714.

[8]. For the use of an alcohol additive to enhance the rate of n-Bu₃SnH regeneration in tin hydride-catalyzed reductive cyclizations, see: D. S. Hays; G. C. Fu, J. Org. Chem. 1996, 61, 4–5.

[9]. a) E. F. V. Scriven, Chem. Soc. Rev. 1983, 12, 129–161. b) A full equivalent of amine is needed (in practice, more is employed) to drive the reaction to completion as it is used up during the course of the reaction. Therefore, we refer to the amine as a promoting agent, not as a catalyst.

[10]. C. A. Willoughby; S. L. Buchwald, J. Am. Chem. Soc. 1994, 116, 8952–8965.

[11]. Burk and co-workers observed a similar effect in the DuPHOS-Rh catalyzed hydrogenation of (E)- and (Z)-enamides, see: M. J. Burk; J. E. Feaster; W. A. Nugent; R. L. Harlow, J. Am. Chem. Soc. 1993, 115, 10125–10138.

[12]. a) M. T. Reding; S. L. Buchwald, J. Org. Chem. 1995, 60, 7784–7890. b) J. Lipowitz; S. A. Bowman, J. Org. Chem. 1973, 38, 162–165. c) S. W. Breeden; N. J. Lawrence, Synlett 1994, 833–835.

[13]. Activation of the catalyst with PMHS was not successful, therefore a small amount of PhSiH₃ was employed. (Catalyst: PhSiH₃, 1:4)

[14]. Some mechanistic similarities exist between this process and that of the asymmetric dihydroxylation of olefins. See: J. S. M. Wai; I. Markó; J. S. Svendsen; M. G. Finn; E. N. Jacobsen; K. B. Sharpless, J. Am. Chem. Soc. 1989, 111, 1123–1125.

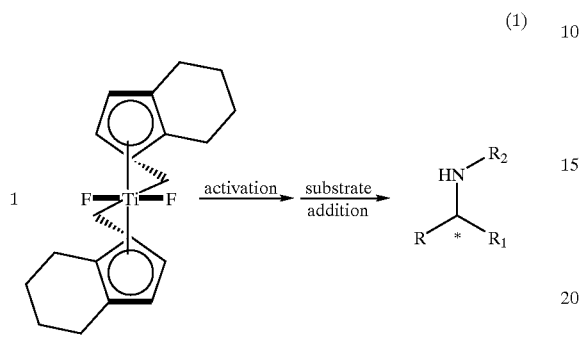

(1)

TABLE 1

Catalytic reduction with different primary amines as promoters.[a]

| Entry | Silane | Added amine[b] | Imine | T (° C.) | Time | % Conv. | % ee | |
|---|---|---|---|---|---|---|---|---|
| 1 | PhSiH$_3$ | — | 2 | r.t. | 12 h[c] | 100 | 97 | 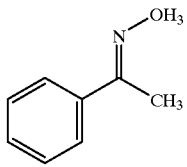 2 |
| 2 | PhSiH$_3$ | — | 3 | 60 | 96 h[d] | 55 | 47 | |
| 3 | PMHS | — | 2 | 60 | 48 h[b] | 50 | — | |
| 4 | PMHS | — | 4 | 60 | 24 h | 5 | — | 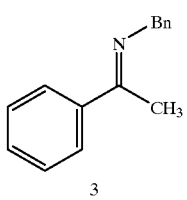 3 |
| 5 | PMHS | n-HexNH$_2$ | 4 | 60 | 2 h | 100 | 85 | |
| 6 | PMHS | tert-BuNH$_2$ | 4 | 60 | 24 h | 39 | — | |
| 7 | PMHS | pyrrolidine | 4 | 60 | 24 h | 4 | — | 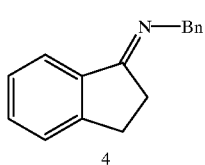 4 |
| 8 | PMHS | iso-BuNH$_2$ | 4 | 60 | 2 h | 100 | 92 | |
| 9 | PMHS | (±)-sec-BuNH$_2$ | 4 | 60 | 2 h | 75 | 78 | |

[a]Unless otherwise noted reactions were run using 5 mol % (S,S)-(EBTHI)TiF$_2$.
[b]Amines were added during a period of 80 min using a syringe pump.
[c]1 mol % catalyst.
[d]10 mol % catalyst.

TABLE 2
Amine promoted catalytic asymmetric reduction of acyclic imines
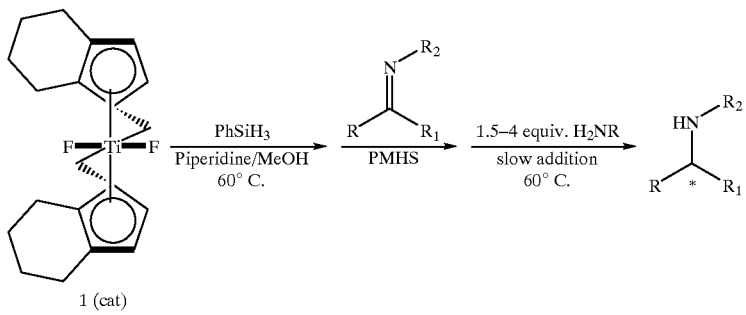
| Entry | Imine | E/Z ratio[a] | mol % cat. | Silane | Amine | Yield (%)[b] | ee (%) |
|---|---|---|---|---|---|---|---|
| 1 | | >50/1 | 1 | PMHS | iso-butyl | 96 | 92[e] |
| 2 | | 15/1 | 0.5 | PMHS | iso-butyl | 95 | 98[c,e] |
| 3 | | 15/1 | 0.5 | PMHS | iso-butyl | 92 | 99[e] |
| 4 | | 18/1 | 2<br>1 | PhSiH₃<br>PMHS | sec-butyl<br>iso-butyl | 88<br>97 | 96[d]<br>98 |
| 5 | | 20/1 | 2<br>0.05 | PhSiH₃<br>PMHS | sec-butyl<br>iso-butyl | 73<br>96 | 93[d]<br>98 |
| 6 | | 23/1 | 0.5 | PMHS | iso-butyl | 96 | 91[c,e] |

TABLE 2-continued

Amine promoted catalytic asymmetric reduction of acyclic imines

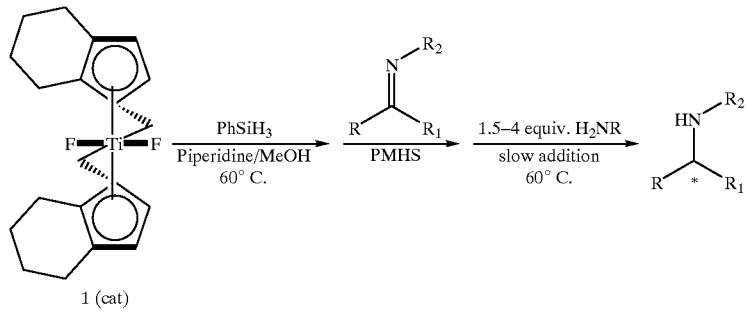

| Entry | Imine | E/Z ratio[a] | mol % cat. | Silane | Amine | Yield (%)[b] | ee (%) |
|-------|-------|--------------|------------|--------|-------|--------------|--------|
| 7 | 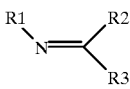 | 3.5/1 | 1 | PMHS | iso-butyl | 96 | 69[d] |
| 8 |  | 2.5/1 | 5 | PMHS | iso-butyl | 85 | 93[c,f] |
| 9 |  | 1.8/1 | 1 | PhSiH$_3$ | iso-butyl | 90 | 97[f] |

Footnotes for Table 2
[a]ratio of E/Z isomers calculated by $^1$H NMR.
[b]Yields refer to isolated compounds of >95% purity as determined by GC and 1H NMR.
[c]Product amines possess S absolute configuration as determined by polarimetry.
[d]Enantiomeric excess (% ee) determined by chiral GC (Chlraldex B-PH, Chlraldex G-TA columns).
[e]Enantiomeric excess (% ee) determined by chiral HPLC on a Chiralcel OD column.
[f]Enantiomeric excess (% ee) determined by $^1$H NMR analysis of the diastereomeric salts resulting from the addition of (R) or (S)-O-acetylmandelic acid.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for synthesizing a secondary amine comprising, combining, in a reaction mixture, a substrate imine, a nucleophilic activator, a silane, and a metal catalyst under conditions wherein the catalyst catalyzes the reduction of the substrate imine by a hydrosilylation reaction.

2. The method of claim 1, wherein said substrate imine is represented by the general formula:

$$\underset{R1}{\phantom{x}}\overset{\phantom{x}}{N}=\underset{R3}{\overset{R2}{\phantom{x}}}$$

wherein

R1, R2 and R3 each independently represent alkyl, alkenyl, alkynyl, carbonyl, thiocarbonyl, acyl, aldehyde, amino, acylamino, amido, amidino, cyano, sulfonyl, sulfoxido, sulfate, sulfonate, sulfamoyl, sulfonamido, phosphoryl, phosphonate, phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, protected versions of any of the above, or a solid or polymeric support;

R$_8$ represents independently for each occurrence aryl, aralkyl, cycloalkyl, cycloalkenyl, or heterocyclyl;

one of R2 or R3 can be a hydrogen;

any two of R1, R2 and R3, taken together, can form a ring, which ring may be a monocyclic or polycyclic carbocycle or heterocycle; and n and m are independently for each occurrence zero or an integer in the range of 1 to 6.

3. The method of claim 2, wherein R1, R2 and R3 each independently represent alkyl, alkenyl, alkynyl, or —(CH$_2$)$_m$—R8.

4. The method of claim 2, wherein R2 and R3 are not identical.

5. The method of claim 2, wherein R1 does not form a conjugated system with the double bond of the imine.

6. The method of claim 2, wherein R1 is alkyl or —(CH$_2$)$_m$—R$_8$.

7. The method of claim 1, wherein said substrate imine is represented by the general formula:

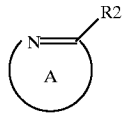

wherein

A represents a substituted or unsubstituted ring selected from the group consisting of monocyclic and polycyclic cycloalkyl, cycloalkenyl, aryl, and heterocyclic rings;

R2 is hydrogen, alkyl, alkenyl, alkynyl, carbonyl, thiocarbonyl, acyl, aldehyde, amino, acylamino, amido, amidino, cyano, sulfonyl, sulfoxido, sulfate, sulfonate, sulfamoyl, sulfonamido, phosphoryl, phosphonate, phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R$^8$, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R8, protected versions of any of the above, or a solid or polymeric support;

R$_8$ represents independently for each occurrence aryl, aralkyl, cycloalkyl, cycloalkenyl, or heterocyclyl; and n and m are independently for each occurrence zero or an integer in the range of 1 to 6.

8. The method of claim 7, wherein R2 represents alkyl, alkenyl, alkynyl, or —(CH$_2$)$_m$—R$_8$.

9. The method of claim 7, wherein A does not form a conjugated system with the double bond of the imine.

10. The method of claim 1, wherein the nucleophilic activator comprises a Lewis basic atom selected from the group consisting of the elements of Groups 15 and 16 of the Periodic Table.

11. The method of claim 10, wherein the nucleophilic activator comprises a Lewis basic atom selected from the group consisting of nitrogen, phosphorous, oxygen and sulfur.

12. The method of claim 11, wherein the nucleophilic activator comprises a Lewis basic nitrogen atom.

13. The method of claim 12, wherein the nucleophilic activator is represented by the general formula:

wherein

R4 represents alkyl, alkenyl, alkynyl, carbonyl, thiocarbonyl, acyl, aldehyde, amino, acylamino, amido, amidino, cyano, sulfonyl, sulfoxido, sulfate, sulfonate, sulfamoyl, sulfonamido, phosphoryl, phosphonate, phosphinate, —(CH$_2$)$_m$—R8, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R8, —(CH$_2$)$_m$—SH, (CH$_2$)$_m$—S-lower alkyl, —(CH$_2$)$_m$—S-lower alkenyl, —(CH$_2$)$_m$—S—(CH$_2$)$_n$—R8, protected versions of any of the above, or a solid or polymeric support;

R$_8$ represents independently for each occurrence aryl, aralkyl, cycloalkyl, cycloalkenyl, or heterocyclyl; and n and m are independently for each occurrence zero or an integer in the range of 1 to 6.

14. The method of claim 13, wherein R4 represents alkyl.

15. The method of claim 14, where R4 represents hexyl.

16. The method of claim 1, wherein said metal catalyst comprises titanium.

17. The method of claim 1 or 16, wherein said metal catalyst is chiral and non-racemic.

18. The method of claim 16, wherein the metal catalyst is ethylene-bis($\eta^5$-tetrahydroindenyl)titanium difluoride.

19. The method of claim 18, wherein the metal catalyst is (S,S)-ethylene-bis($\eta^5$-tetrahydroindenyl)titanium difluoride.

20. The method of claim 1, wherein said silane is represented by the general formula:

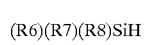

wherein

R6 represents alkyl, alkenyl, alkynyl, carbonyl, thiocarbonyl, acyl, aldehyde, amino, acylamino, amido, amidino, cyano, sulfonyl, sulfoxido, sulfate, sulfonate, sulfamoyl, sulfonamido, phosphoryl, phosphonate, phosphinate, —(CH$_2$)$_m$—R80, —(CH$_2$)$_m$—OH, —(CH$_2$)$_m$—O-lower alkyl, —(CH$_2$)$_m$—O-lower alkenyl, —(CH$_2$)$_m$—O—(CH$_2$)$_n$—R80, —(CH$_2$)$_m$—SH, —(CH$_2$)$_m$—S-lower alkyl, —(CH$_2$)$_m$—S-lower alkenyl, —(CH$_2$)$_m$—S—(CH$_2$)$_n$—R80, protected versions of any of the above, or a solid or polymeric support;

R7 and R8 each independently represent hydrogen, alkyl, alkenyl, alkynyl, carbonyl, thiocarbonyl, acyl, aldehyde, amino, acylamino, amido, amidino, cyano, sulfonyl, sulfoxido, sulfate, sulfonate, sulfamoyl, sulfonamido, phosphoryl, phosphonate, phosphinate, —$(CH_2)_m$—R80, —$(CH_2)_m$—OH, —$(CH_2)_m$—O-lower alkyl, —$(CH_2)_m$—O-lower alkenyl, —$(CH_2)_m$—O—$(CH_2)_n$— R80, —$(CH_2)_m$—SH, —$(CH_2)_m$—S-lower alkyl, —$(CH_2)_m$—S-lower alkenyl, —$(CH_2)_m$—S—$(CH_2)_n$—R80, protected versions of any of the above, or a solid or polymeric support;

$R_{80}$ represents independently for each occurrence aryl, aralkyl, cycloalkyl, cycloalkenyl, or heterocyclyl; and n and m are independently for each occurrence zero or an integer in the range of 1 to 6.

21. The method of claim 20, wherein R7 and R8 represent hydrogen.

22. The method of claim 20 or 21, wherein R6 represents alkyl, alkenyl or aryl.

23. The method of claim 22, wherein R6 represents phenyl.

24. The method of claim 1, wherein said silane is polymethylhydrosiloxane (PMHS).

* * * * *